(12) United States Patent
Gao et al.

(10) Patent No.: US 11,774,435 B2
(45) Date of Patent: Oct. 3, 2023

(54) DIGITAL SAMPLE PLOT FOR SOIL FAUNA IN DRY LAND AND CONSTRUCTION METHOD THEREOF

(71) Applicant: Ningbo University, Zhejiang (CN)

(72) Inventors: Meixiang Gao, Zhejiang (CN); Tingyu Lu, Zhejiang (CN); Jinwen Liu, Zhejiang (CN); Lu Dai, Zhejiang (CN); Hao Xu, Zhejiang (CN)

(73) Assignee: NINGBO UNIVERSITY, Zhejiang (CN)

( * ) Notice: Subject to any disclaimer, the term of this patent is extended or adjusted under 35 U.S.C. 154(b) by 47 days.

(21) Appl. No.: 17/489,745

(22) Filed: Sep. 29, 2021

(65) Prior Publication Data
US 2022/0214325 A1 Jul. 7, 2022

(30) Foreign Application Priority Data
Jan. 5, 2021 (CN) .......................... 202110008419.1

(51) Int. Cl.
*G01N 33/24* (2006.01)
*G01D 21/02* (2006.01)
*G01W 1/02* (2006.01)
*H04N 23/90* (2023.01)

(52) U.S. Cl.
CPC ............. *G01N 33/24* (2013.01); *G01D 21/02* (2013.01); *G01W 1/02* (2013.01); *H04N 23/90* (2023.01)

(58) Field of Classification Search
CPC ............. G01N 33/24; G01N 2033/243; G01N 2033/245; G01N 1/2294; G01N 2001/021; G01N 1/02; G01D 21/02; H04N 23/90; G01W 1/02; G06T 2207/30181; Y10S 71/903; Y10S 106/90; Y10T 137/189; G01K 17/08
See application file for complete search history.

(56) References Cited

U.S. PATENT DOCUMENTS

| | | | |
|---|---|---|---|
| 2015/0185196 A1* | 7/2015 | Coram | A01C 21/00 73/865.6 |
| 2019/0017984 A1* | 1/2019 | Fang | G01J 3/2823 |
| 2020/0257997 A1* | 8/2020 | Mewes | A01G 22/00 |

FOREIGN PATENT DOCUMENTS

GB   2582610 A * 9/2020 ............. A01B 76/00

OTHER PUBLICATIONS

Liam Donnelly et al., Above- and below-ground biomass partitioning and fine root morphology in juvenile Sitka spruce clones in monoclonal and polyclonal mixtures, Forest Ecology and Management, Apr. 2016, pp. 17-25, vol. 373, Elsevier.
Donald S. Ross et al., Impact of an Extreme Storm Event on River Corridor Bank Erosion and Phosphorus Mobilization in a Mountainous Watershed in the Northeastern United States, Journal of Geophysical Research: Biogeosciences, Jan. 4, 2019, pp. 18-32, vol. 124.

(Continued)

*Primary Examiner* — Daniel R Miller
*Assistant Examiner* — Eric Sebastian Von Wald

(57) ABSTRACT

The invention discloses a digital sample plot for soil fauna in dry land and the construction method thereof, comprising the dry land with sample plots in the center, automatic monitoring equipment and power supply equipment; such equipment is set around, underground, on the surface of or above the sample plot; the invention realizes a full-coverage, all-weather and three-dimensional sample plot.

8 Claims, 1 Drawing Sheet

(56) References Cited

OTHER PUBLICATIONS

Tuomas Yrttimaa et al., Structural Changes in Boreal Forests Can Be Quantified Using Terrestrial Laser Scanning, Remote Sensing, Aug. 20, 2020, pp. 1-20, vol. 12, Issue 2672.
David E. Brown et al., Digitized Map of Biotic Communities for Plotting and Comparing Distributions of North American Animals, The Southwestern Naturalist, Dec. 2007, pp. 610-617, vol. 52, No. 4.
János Podani et al., Individual-centered analysis of mapped point patterns representing multi-species assemblages, Journal of Vegetation Science, 1997, pp. 259-270, vol. 8.
Atsalek Rattanawannee et al., Geometric morphometric analysis of giant honeybee (Apis dorsata Fabricius, 1793) populations in Thailand, Journal of Asia-Pacific Entomology, Jul. 2012, pp. 611-618, vol. 15, Elsevier.
Potjamas Chuangchang et al., Modelling urban growth over time using grid-digitized method with variance inflation factors applied to spatial correlation, Arabian Journal of Geosciences, Apr. 21, 2016, pp. 1-13, vol. 9, Issue 342, Springer.
Marc Lesturgie et al., A new technique to characterize foliage attenuation using passive radar in the L-band, Comptes Rendus Physique, Aug. 27, 2016, pp. 1003-1017, vol. 17, Elsevier.
Markus Holopainen et al., Accuracy of digitized aerial photographs for assessing forest habitats at plot level, Scandinavian Journal of Forest Research, 1998, pp. 499-508, vol. 13, Issue 1-4.
Nataliya Kuznetsova et al., Diversity of Collembola under various types of anthropogenic load on ecosystems of European part of Russia, Biodiversity Data Journal, Oct. 30, 2020, pp. 1-15, vol. 8, Issue e58951.
Ananta Man Singh Pradhan et al., GIS-based landslide susceptibility model considering effective contributing area for drainage time, Geocarto International, Mar. 20, 2017, pp. 810-829, vol. 33, No. 8, Taylor & Francis.
Susan K. Wiser, Achievements and challenges in the integration, reuse and synthesis of vegetation plot data, Journal of Vegetation Science, 2016, pp. 868-879, vol. 27.
Hamid Gholizadeh et al., Hyrcanian Forest Vegetation Database, Phytocoenologia, Dec. 2018, pp. 209-210, vol. 49, Issue 2.
T. C. Nxele et al., Studying Earthworms (Annelida: Oligochaeta) in South Africa, African Invertebrates, Dec. 29, 2015, pp. 779-806, vol. 56, Issue 3, KwaZulu-Natal Museum.

\* cited by examiner

DIGITAL SAMPLE PLOT FOR SOIL FAUNA IN DRY LAND AND CONSTRUCTION METHOD THEREOF

CROSS REFERENCE TO RELATED APPLICATIONS

The present application claims the benefit of Chinese Patent Application No. 202110008419.1 filed on Jan. 5, 2021, the contents of which are incorporated herein by reference in their entirety.

TECHNICAL FIELD

The invention belongs to the soil fauna research technical field, specifically relating to a digital sample plot for soil fauna in dry land and construction method thereof.

BACKGROUND

In the research of soil fauna in dry land, the construction and monitoring of long-term fixed monitoring sample plots are quite important platforms and means. At present, small or large long-term fixed monitoring sample plots are often used, which are of different sizes, and traditional investigation methods are used to collect samples of soil fauna, such as soil column, hand-picking, trap, observation, suction trap, and electric shock, and several dynamic investigations and monitoring are implemented regularly or irregularly. The current soil fauna investigation is carried out by selecting a part of sampling points within the sample plot. Even if more sampling points are set, it is impossible to monitor all soil fauna samples in all spatial ranges and at all spatial scales in the whole sample plot at an omnidirectional and non-dead angle.

Existing monitoring investigations often collect soil fauna samples at intervals of weeks, months, etc. The reasons for the time interval are as follows: (1) limited by large field workload, multiple dynamic sampling will bring a larger field workload, which will lead to heavy indoor identification and other related workloads, but many laboratories and scientific research teams are unable to complete such heavy tasks, so they choose to adopt the strategy of sampling at certain intervals to reduce the workload; (2) most of the traditional sampling methods are destructive (that is, non-environment-friendly). Repeated and frequent sampling will cause great damage to the sample plots and change the soil environmental conditions in the sample plots, thus changing the ecology, activity and other behaviors of soil fauna. Dynamic investigation and monitoring in this context may collect unreal, non-in-situ data disturbed by human beings. (3) Traditional sampling methods will basically cause the death of individual soil fauna, so it is necessary to bring the dead and stereotyped samples back to the laboratory for identification and analysis, which is not conducive to the protection and maintenance of biodiversity. For those rare or endangered soil fauna species, it is a great threat.

Some precious data still cannot be monitored by existing methods. For instance, in the existing investigation methods, if soil fauna samples are collected a few days after pesticide spraying, only the soil fauna data after spraying for a period of time can be obtained, thus in terms of technical means, it is impossible to monitor the real-time and real response and activity status of soil fauna after pesticide spraying. For example, data for the following research questions cannot be obtained: after spraying pesticides, which soil faunas escape first, which soil faunas escape last, and which soil faunas do not escape but have a strong tolerance, which soil faunas return to the sample plot on what day, at what time period and under what weather conditions.

SUMMARY

In view of the shortcomings of the prior art, the invention provides the digital sample plot for soil fauna in dry land and construction method thereof.

For the purpose above, the invention adopts the following technical solution:

a digital sample plot for soil fauna in dry land, comprises at least one dry land that can be used for a long time, automatic monitoring equipment, and power supply equipment, wherein the distance between each dry land is more than 200 m; each dry land is set up with a square sample plot at the center; the sample plot has a certain distance from the edge of the dry land to avoid edge effects; permanent landmarks are respectively set at the four corners of the sample plot according to the geographical position, or a fence is set at the boundary of the dry land where the sample plot is located; the interior of each sample plot is divided into several square grids with basic units;

the above automatic monitoring equipment includes a plurality of HD cameras, a soil multi-parameter measuring instrument, an automatic temperature and humidity monitor, a sound monitoring recorder and a small agricultural meteorological station;

a plurality of the HD cameras consist of underground HD cameras, surface HD cameras and above-ground HD cameras, of which the underground HD cameras are respectively set up at a certain depth or multiple depths in the underground soil of the sample plot to monitor the behaviors of underground soil faunas in real time; the surface HD cameras are arranged on the surface of the sample plot to monitor the behaviors of surface soil faunas in real time, with a monitoring range of at least 1 m×1 m, and the resolution of monitoring surface soil faunas of 1.0 cm; the above-ground HD cameras are set at a height of 0.2 m-1 m above the surface of the sample plot to monitor the behaviors of faunas on crops or weeds in real time, and the actual setting height depends on the monitored crop species and height; the soil multi-parameter measuring instruments are respectively set at a certain depth or multiple depths of the underground soil of the sample plot to monitor the dynamic data of underground soil temperature, humidity, salinity and in-situ pH value in real time, and the soil multi-parameter measuring instrument is set to be close to the corresponding underground HD camera; the automatic temperature and humidity monitor is arranged on the surface of the sample plot to monitor the dynamic data of surface temperature and humidity in real time; the sound monitoring recorder is arranged on the surface of the sample plot, and at least two sound monitoring recorders are arranged on the surface of the sample plot to monitor fauna sound data; the small agricultural meteorological station is arranged on the ground of the sample plot to monitor the meteorological factor data on the ground in real time;

the power supply equipment comprises a main power supply equipment and standby power supply equipment; the main power supply equipment adopts solar panels, and the standby power supply equipment adopts agricultural or industrial power near the sample plot.

Furthermore, the area of the sample plot is 20 m×20 m, and the distance between the boundary of the sample plot and the edge of the dry land is at least 10 m.

Furthermore, the dry land is arranged at a farmland ecological station or a location not far from the village in order to obtain standby power supply; meanwhile, the dry land is far away from roads, railways, buildings, ponds and livestock and poultry breeding sites, to reduce external interference to the sample plot.

Furthermore, the dry land can be used for more than 10-20 years for monitoring and related investigations and researches to ensure that important data can be obtained from the sample plot for the long term.

Furthermore, the automatic monitoring equipment also includes an anemometer and an irradiatometer to monitor the dynamic data of surface wind speed and irradiance in real time.

Furthermore, the fence is square surrounded by a number of vertical railings, and the distance between the fence and the boundary of the sample plot is at least 10 m, and the distance between the two adjacent railings is at least 0.1 m, to ensure normal ventilation in the sample plot, make no changes to the data of meteorological factors in the sample plot, and make no influence on the normal activities of soil fauna in the sample plot on the one hand, and to prevent the entry of other larger animals or human beings to avoid the unexpected damage to the sample plot on the other hand.

Furthermore, the basic unit of the grid is 0.1 m×0.1 m, and the sample plot with an area of 20 m×20 m is divided into 40,000 grids.

Furthermore, the soil multi-parameter measuring instrument is set within a range of less than 0.1 m in the horizontal direction from the underground HD camera.

The invention provides a method for the construction of a digital sample plot for soil fauna in dry land, including the following steps:

Step 1, selection of sample plot in dry land at field: one or more dry lands are selected for sample plot construction according to the experimental purpose, and the distance between different sample plots is ensured to be more than 200 m;

Step 2, delineation of digital boundary of the sample plot in dry land: the GPS or Beidou Navigation Positioning Technology is applied to measure the square sample plot in the center of the selected dry land, and temporary landmarks are inserted on the four boundaries of the sample plot, so as to accurately delineate the digital boundary of the sample plot;

Step 3, setting of permanent landmarks or fences at the boundary of the sample plot in dry land: if the sample plot is located in the farmland ecological station, permanent landmarks only need to be set at the four corners of the sample plot; if the sample plot is located outside the ecological station and there are no facilities for protection, a fence should be set up outside the sample plot for protection;

Step 4, measurement of the digital grid of sample plot in dry land: the GPS or Beidou Navigation Positioning Technology is applied to divide the delineated sample plot into several grids in the basic unit;

Step 5, setting of HD cameras at a certain depth or multiple depths in the underground soil to monitor the behaviors of underground soil faunas in real time;

Step 6, setting of the soil multi-parameter measuring instrument at a certain depth or multiple depths in the underground soil to monitor the dynamic data of temperature, humidity, salinity and in-situ pH value of underground soil in real time;

Step 7, setting of HD cameras on the surface to monitor the behaviors of surface soil fauna in real time;

Step 8, setting of the automatic temperature and humidity monitor, anemometer and irradiatometer on the surface to obtain surface temperature, humidity, wind speed, irradiance and other meteorological parameters;

Step 9, setting of HD cameras at a height of about 0.2 m-1 m from the ground surface to monitor the behaviors of faunas on crops or weeds in real time;

Step 10, setting of the sound monitoring recorder on the surface to monitor fauna sound data;

Step 11, installation of the small agricultural meteorological station on the ground to monitor the data of meteorological factors on the ground in real time; and Step 12, connection of the power supply equipment of the sample plot and inspection several times.

Beneficial Effects of the Invention:

First, there is no need to use traditional tedious and non-environment-friendly methods such as digging soil columns and arranging traps to collect samples of soil fauna, which can reduce the damage to the background soil environment of the sample plot, keep the original soil environment to the maximum extent, and ensure the collection of in-situ samples with the least disturbance to the maximum extent, really achieving the environment-friendly sample collection method that the academic community is trying to explore. This will greatly promote the digitization, automation and intelligence of soil fauna sample collection in dry land.

Second, the monitoring of living animals is directly carried out by arranging cameras, sound monitoring recorders and other instruments and equipment to monitor the most direct and authentic firsthand data such as the number, moving direction, moving speed, predation, competition and mating of soil fauna in dry land, which will not cause disturbance and influence to the soil fauna themselves, will not cause the death of soil fauna, but contribute to the protection of soil biodiversity;

Third, the most authentic firsthand data of soil fauna in the wild can be obtained uninterruptedly and continuously in real time for 24 successive hours;

Fourth, three-dimensional investigation and monitoring can be carried out in multiple spatial dimensions, and instruments and equipment can be arranged in underground soil, on surface soil and above-ground plants respectively, and the three-dimensional soil fauna data of "underground, surface and aboveground" can be monitored and obtained;

Fifth, investigation and monitoring with full spatial coverage can be achieved, for instance, for the sample plot of 20 m×20 m, if the monitoring range of an HD camera is 2 m×2 m, then 100 cameras can fully monitor and obtain the activities of all soil faunas in the whole range of 400 m$^2$ without any dead corners;

Sixth, simultaneous, real-time and intelligent monitoring of environmental factors, including soil, meteorology, crops, weeds and other animals such as pests, can be carried out at the same time.

Seventh, this digital sample plot is applied as a platform to monitor and evaluate the process and effect of the analog control experiment in real time, and the important data which cannot be monitored by traditional methods can be obtained.

Figure 1:
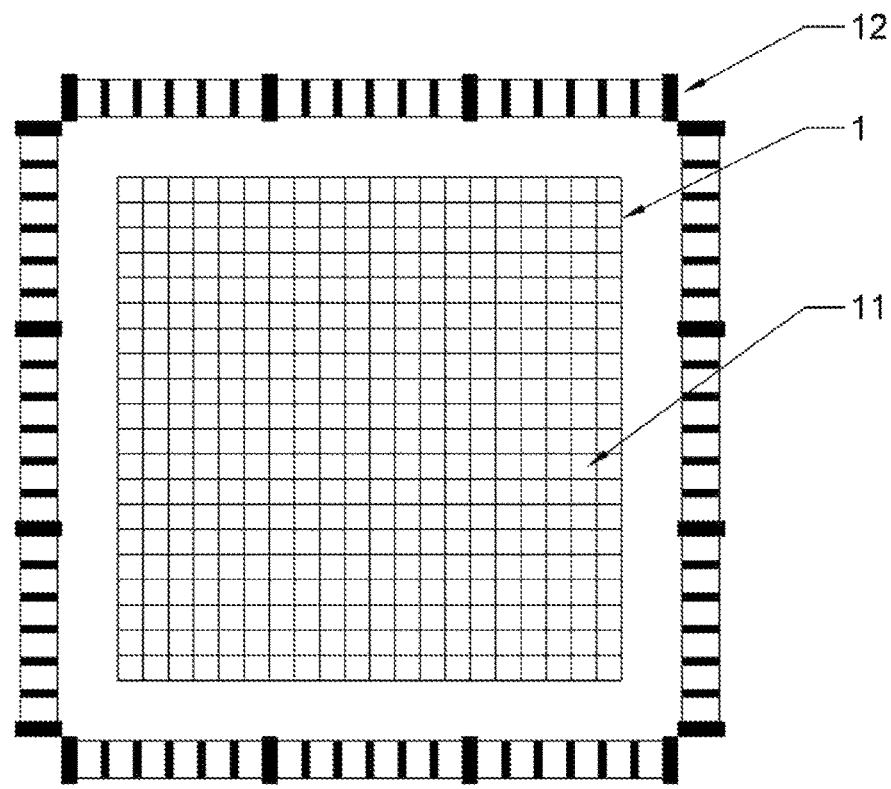
FIG. 1 is a top view of a partial structure of digital sample plot for soil fauna in dry land in the invention.

In the drawings, 1—sample plot, 2—HD camera, 3—soil multi-parameter measuring instrument, 4—sound monitoring recorder, 5—small agricultural meteorological station; 11—grid, 12—fence,
21—underground HD camera, 22—surface HD camera, 23—aboveground HD camera.

DETAILED DESCRIPTION

The invention is illustrated by referring to specific embodiments below. Those skilled in the art can understand that these embodiments are used only to illustrate the invention and do not limit the scope of the invention in any way.

A digital sample plot for soil fauna in dry land, comprises a dry land that can be used for more than 10-20 years, automatic monitoring equipment and power supply equipment, wherein the dry land is arranged at a farmland ecological station or a location not far from the village in order to obtain standby power supply and is far away from roads, railways, buildings, ponds and livestock and poultry breeding sites to reduce external interference to the sample plot, with an area of above 30 m×30 m. As shown in FIG. 1, there is a square sample plot 1 in the center of the dry land; the area of sample plot 1 is 20 m×20 m, and the sample plot 1 is 10 m away from the edge of the dry land, to avoid the edge effect. In this embodiment, sample plot 1 is located outside the ecological station and not provided with protection facilities. The boundary of dry land where sample plot 1 is located is provided with a fence 12, which is in square surrounded by several vertical railings. The distance between fence 12 and the boundary of sample plot 1 is at least 10 m, and the distance between the two adjacent railings is at least 0.1 m, on the one hand, to ensure normal ventilation in the sample plot, make no changes to the meteorological environment of the sample plot, and make no influence on the normal activities of soil fauna in the sample plot, and on the other hand, to prevent the entry of other larger animals or human beings to avoid the unexpected damage to the sample plot. The interior of sample plot 1 is divided into several square grids 11 with the basic unit; the basic unit of grid 11 is 0.1 m×0.1 m, and the sample plot with an area of 20 m×20 m is divided into 40,000 grids.

Figure 2:
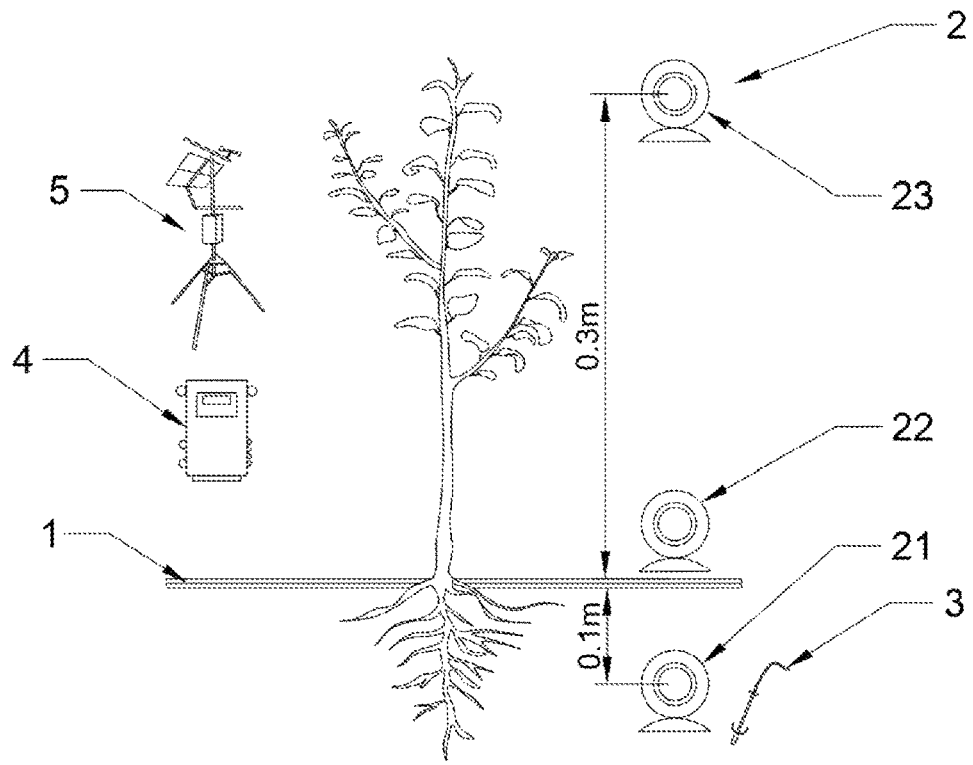
FIG. 2 is a structural schematic diagram of the digital sample plot for soil fauna in dry land in the invention.

As shown in FIG. 2, the automatic monitoring equipment includes a plurality of HD cameras 2, soil multi-parameter measuring instrument 3, automatic temperature and humidity monitor (not shown), anemometer (not shown), irradiatometer (not shown), sound monitoring recorder 4 and small agricultural meteorological station 5; specifically:

An underground HD camera 21 is set at the depth of 0.1 m in the underground soil of sample plot 1 to monitor behaviors of underground soil fauna in real time; meanwhile, a soil multi-parameter measuring instrument 3 is set at the depth of 0.1 m in the underground soil of sample plot 1 to monitor the dynamic data of temperature, moisture, salinity and in-situ pH value of underground soil in real time, and is set near underground HD camera 21 and within 0.10 m from underground HD camera 21 in the horizontal direction;

A surface HD camera 22 is set on the surface of sample plot 1 to monitor the behaviors of surface soil fauna in real time; meanwhile, the automatic temperature and humidity monitor (not shown), anemometer (not shown) and irradiatometer (not shown) are set on the surface to monitor dynamic data of surface temperature, humidity, wind speed, and irradiance in real time; 2-4 sound monitoring recorders 4 are set in the sample plot with an area of 20 m×20 m evenly to monitor sound data of fauna;

An above-ground HD camera 23 is set at a height of 0.3 m from the ground of sample plot 1 to monitor the behaviors of fauna on corps and weeds in real time; a small agricultural meteorological station 5 is set on the ground to monitor data of above-ground meteorological factors in real time;

The power supply equipment comprises a main power supply equipment and standby power supply equipment; the main power supply equipment adopts solar panels, and the standby power supply equipment adopts agricultural or industrial power near the sample plot.

A method for the construction of a digital sample plot for soil fauna in dry land, including the following steps:

Step 1, selection of sample plot in dry land at field, specifically: One or more dry lands are selected for sample plot construction according to the experimental purpose, and the distance between different sample plots is ensured to be more than 200 m. In this embodiment, the digital sample plot for soil fauna in dry land with an area of 20 m×20 m is taken as an example, and the requirements for the selection of dry land are as follows:

(1) The sample plot is square, and its area is above 30 m×30 m in order to avoid edge effects;
(2) The sample plot is set at a farmland ecological station or a location not far from the village to obtain standby power supply for automatic monitoring of instruments and equipment;
(3) The sample plot is far away from roads, railways, buildings, ponds, livestock and poultry breeding sites, etc. to reduce external interference to the sample plot;
(4) The sample plot can be used for more than 10-20 years for monitoring and related investigations and researches to ensure that important data can be obtained from the sample plot for the long term;

Step 2, delineation of digital boundary of the sample plot in dry land, specifically:

The GPS or Beidou Navigation Positioning Technology is applied to measure the sample plot with an area of 20 m×20 m in the center of the selected dry land, and temporary landmarks, such as PVC pipes, are inserted on the four boundaries of the sample plot, so as to accurately delineate the digital boundary of the sample plot;

Step 3, setting of permanent landmarks or fences at the boundary of the sample plot in dry land, specifically:

(1) If the sample plot is located in the farmland ecological station, permanent landmarks, such as cement piles with marks and instructions, only need to be set at the four corners of the sample plot, and no iron fence around the perimeter is needed;
(2) If the sample plot is located outside the ecological station and there are no facilities for protection, a fence should be set up outside the sample plot for protection; the square enclosed by the fence is of an area of 30 m×30 m at least. Enough width between the railings of the fence is provided, and the distance between the two railings is at least 0.1 m, on the one hand, to ensure normal ventilation in the sample plot, make no changes to the microclimate environment of the sample plot, and make no influence on the normal activities of soil fauna in the sample plot, and on the other hand, to prevent the entry of other larger animals or human beings to avoid the unexpected damage to the sample plot.

Step 4, measurement of the digital grid of sample plot in dry land, specifically: The GPS or Beidou Navigation Positioning Technology is applied to divide the delineated sample plot into 40,000 grids in a unit of 0.1 m×0.1 m. Errors for the boundary lines and crossing points of these 0.1 m×0.1 m digital sample plots are controlled within 3-4 cm. In this embodiment, these digital sample plots are taken as the basic unit to assist in the subsequent intelligent computing of the activities and behaviors of soil fauna, such as moving direction, moving angle, and moving speed.

Step 5, setting of HD cameras in the underground soil to monitor the behaviors of underground soil fauna in real time, specifically:

Set HD cameras at a certain depth or multiple depths in the underground soil, for example, set HD cameras at a distance of 0.1 m below the ground, or set cameras at distances of 0.05 m, 0.1 m, 0.15 m, and 0.2 m below the ground respectively;

Step 6, setting of the soil multi-parameter measuring instrument underground to monitor the dynamic data of temperature, humidity, salinity and in-situ pH value of underground soil in real time, specifically:

Set the soil multi-parameter measuring instrument and other instruments and equipment at a certain depth or multiple depths in the underground soil, where the setting position is close to the position of the HD camera in step 5, but not next to the camera, and the distance from the HD camera should be less than 0.05 m in the horizontal direction. In this way, dynamic data of soil temperature, humidity, salinity and in-situ pH value that have important effects on soil fauna can be monitored and obtained automatically.

Step 7, setting of HD cameras on the surface to monitor the behaviors of surface soil fauna in real time, specifically:

Set up HD cameras on the surface, where the monitoring range of each camera to the surface must be at least 1 m×m, and the resolution of monitoring surface soil fauna must be 1.0 cm. Please note that the shooting quality will be affected due to image jittering caused by camera shaking under the influence of wind. Therefore, to ensure the stability of HD camera set on the surface, a special surface camera setting frame needs to be customized, and is driven into the soil to a depth of at least 0.5 m and set in the furrows to reduce the impact on normal agricultural activities;

Step 8, setting of the near-surface automatic monitoring equipment on the surface, specifically:

Set the automatic temperature and humidity monitor on the surface, as well as monitoring equipment such as anemometers and irradiatometers to obtain the temperature, humidity, wind speed, irradiance and other meteorological parameters of the surface;

Step 9, setting of HD cameras above the ground to monitor the behaviors of fauna on crops or weeds in real time, specifically:

Set an HD camera at a height of about 0.2 m-1 m from the surface, and the actual height depends on the monitored crop species and height. The camera is used to monitor agricultural insects such as arthropods, pests, beneficial insects on crops and weeds, and monitor the growth rate, leaf area, height, color and other important data of crops and weeds;

Step 10, setting of the sound monitoring recorder on the surface to monitor fauna sound data, specifically:

Set sound monitoring recorders near the surface, and evenly set 2-4 sets in a 20 m×20 m sample plot for day and night monitoring to obtain sound data of birds, beasts, insects and other animals.

Step 11, installation of the small agricultural meteorological station on the ground to monitor the data of meteorological factors on the ground in real time, specifically:

Set a standard small agricultural meteorological station on the ground, and just provide one set in the 20 m×20 m sample plot to monitor atmospheric temperature, humidity, pressure, wind speed, wind direction, irradiance and other parameters near the surface of the sample plot in real time.

Step 12, connection of the power supply equipment of the sample plot and inspection several times, specifically:

The sample plot needs a sufficient, safe, long-lasting, and stable power supply. The power supply for the digital sample plot for soil fauna in dry land mainly comes from solar panels, and its standby power supply is agricultural or industrial power of nearby villages.

What is claimed is:

1. A digital sample plot for soil fauna in dry land, comprising: at least one dry land; automatic monitoring equipment; and power supply equipment, when there are a plurality of dry lands, a distance between two adjacent dry lands is more than 200 m; and each dry land includes a square sample plot at a center of the dry land, wherein the square sample plot has a distance from an edge of the dry land to avoid edge effects; the dry land includes permanent landmarks respectively set at the four corners of the square sample plot according to a geographical position of the square sample plot, or the dry land includes a fence at a boundary of the dry land; and the square sample plot is divided into several square grids with basic units;

the automatic monitoring equipment includes a plurality of HD cameras, soil multi-parameter measuring instruments, an automatic temperature and humidity monitor, sound monitoring recorders and an agricultural meteorological station;

the plurality of HD cameras consist of underground HD cameras, surface HD cameras and above-ground HD cameras, wherein the underground HD cameras are respectively set up at a depth or multiple depths in an underground soil of the square sample plot to monitor behaviors of underground soil faunas in real time; the surface HD cameras are arranged on a surface of the square sample plot to monitor behaviors of surface soil faunas in real time, with a monitoring range of at least 1 m×1 m, and a resolution of monitoring surface soil faunas of 1.0 cm; the above-ground HD cameras are set at a height of 0.2 m-1 m above the surface of the square sample plot to monitor behaviors of faunas on crops or weeds in real time, and an actual setting height depends on a monitored crop species and height;

the soil multi-parameter measuring instrument is respectively set at a depth or multiple depths of the underground soil of the square sample plot to monitor dynamic data of underground soil temperature, humidity, salinity and in-situ pH value in real time;

the automatic temperature and humidity monitor is arranged on the surface of the square sample plot to monitor dynamic data of surface temperature and humidity in real time;

the sound monitoring recorders are arranged on the surface of the square sample plot to monitor fauna sound data; the agricultural meteorological station is arranged on a ground of the square sample plot to monitor a meteorological factor data on the ground in real time; and the power supply equipment comprises a main power supply equipment and standby power supply equipment; the main power supply equipment includes solar panels, and the standby power supply equipment includes agricultural or industrial power near the digital sample plot.

2. The digital sample plot for soil fauna in dry land of claim 1, wherein an area of the square sample plot is 20 m×20 m, and the distance between a boundary of the square sample plot and the edge of the dry land is at least 10 m.

3. The digital sample plot for soil fauna in dry land of claim 1, wherein the dry land can be used for more than 10-20 years for monitoring and related investigations and researches to ensure that important data can be obtained from the square sample plot.

4. The digital sample plot for soil fauna in dry land of claim 1, wherein the automatic monitoring equipment also includes an anemometer and an irradiatometer to monitor dynamic data of surface wind speed and irradiance in real time.

5. The digital sample plot for soil fauna in dry land of claim 1, wherein the fence is square surrounded by a number of vertical railings, and a distance between the fence and a boundary of the square sample plot is at least 10 m, and a distance between two adjacent railings is at least 0.1 m.

6. The digital sample plot for soil fauna in dry land of claim 1, wherein the basic unit of the square grid is 0.1 m×0.1 m, and the square sample plot with an area of 20 m×20 m is divided into 40,000 square grids.

7. The digital sample plot for soil fauna in dry land of claim 1, wherein the soil multi-parameter measuring instrument is set within a range of less than 0.1 m in a horizontal direction from an underground HD camera.

8. A construction method of a digital sample plot for soil fauna in dry land of claim 1, comprising:
Step 1, selection of a sample plot in dry land at field: one or more dry lands are selected for sample plot construction according to an experimental purpose, and the distance between two adjacent dry lands is set to be more than 200 m when more dry lands are selected;
Step 2, delineation of a digital boundary of the sample plot in the dry land: a GPS or Beidou Navigation Positioning Technology is applied to measure one or more square sample plots in the centers of the selected one or more dry lands, and temporary landmarks are inserted on four boundaries of the square sample plot, so as to accurately delineate the digital boundary of the square sample plot;
Step 3, setting of permanent landmarks or fences at the boundary of the sample plot in dry land: when the square sample plot is located in a farmland ecological station, the permanent landmarks are set at four corners of the square sample plot; when the square sample plot is located outside the farmland ecological station and there are no facilities for protection, the fence is set up outside the square sample plot for protection;
Step 4, measurement of the digital grids of the sample plot in dry land: the GPS or Beidou Navigation Positioning Technology is applied to divide the delineated square sample plot into several grids in the basic unit;
Step 5, setting of HD cameras at a depth or multiple depths in the underground soil to monitor the behaviors of underground soil faunas in real time;
Step 6, setting of the soil multi-parameter measuring instrument at a depth or multiple depths in the underground soil to monitor the dynamic data of temperature, humidity, salinity and in-situ pH value of underground soil in real time;
Step 7, setting of HD cameras on the surface to monitor the behaviors of surface soil fauna in real time;
Step 8, setting of the automatic temperature and humidity monitor on the surface to obtain surface temperature and humidity;
Step 9, setting of the above-ground HD cameras at a height of about 0.2 m-1 m from the surface to monitor the behaviors of faunas on crops or weeds in real time;
Step 10, setting of the sound monitoring recorders on the surface to monitor fauna sound data;
Step 11, installation of the agricultural meteorological station on the ground to monitor the data of meteorological factors on the ground in real time; and
Step 12, connection and inspection of the power supply equipment of the digital sample plot.

* * * * *